(12) United States Patent
O'Malley et al.

(10) Patent No.: US 11,021,524 B2
(45) Date of Patent: Jun. 1, 2021

(54) PROTEINS FROM ANAEROBIC FUNGI AND USES THEREOF

(71) Applicant: The Regents of the University of California, Oakland, CA (US)

(72) Inventors: Michelle O'Malley, Santa Barbara, CA (US); Kevin Solomon, Lafayette, IN (US); Charles Haitjema, San Jose, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/898,421

(22) Filed: Jun. 10, 2020

(65) Prior Publication Data

US 2020/0299338 A1    Sep. 24, 2020

Related U.S. Application Data

(63) Continuation of application No. 15/782,016, filed as application No. PCT/US2016/065579 on Dec. 8, 2016, now Pat. No. 10,717,768.

(60) Provisional application No. 62/296,064, filed on Feb. 16, 2016, provisional application No. 62/265,397, filed on Dec. 9, 2015.

(51) Int. Cl.

| | |
|---|---|
| *C12P 21/06* | (2006.01) |
| *C07K 14/37* | (2006.01) |
| *C12N 15/52* | (2006.01) |
| *C12N 9/00* | (2006.01) |
| *C12N 9/24* | (2006.01) |
| *C12P 7/10* | (2006.01) |
| *C12P 21/02* | (2006.01) |
| *C12P 39/00* | (2006.01) |
| *C12N 9/04* | (2006.01) |
| *C12N 15/70* | (2006.01) |
| *C12N 15/81* | (2006.01) |

(52) U.S. Cl.
CPC .............. *C07K 14/37* (2013.01); *C12N 9/00* (2013.01); *C12N 9/24* (2013.01); *C12N 15/52* (2013.01); *C12P 7/10* (2013.01); *C12P 21/02* (2013.01); *C12P 39/00* (2013.01); *C12N 9/0006* (2013.01); *C12N 15/70* (2013.01); *C12N 15/81* (2013.01)

(58) Field of Classification Search
CPC ..................................................... C07K 14/37
See application file for complete search history.

(56) References Cited

U.S. PATENT DOCUMENTS

| | | | |
|---|---|---|---|
| 8,361,752 | B2 | 1/2013 | Kohda et al. |
| 2011/0306105 | A1 | 12/2011 | Chen et al. |

FOREIGN PATENT DOCUMENTS

| | | |
|---|---|---|
| EP | 2410061 A1 | 1/2012 |
| WO | 2015-019346 A1 | 2/2015 |
| WO | 2017100429 A1 | 6/2017 |

OTHER PUBLICATIONS

Rincon, Marco T. et al., "A Novel Cell Surface-Anchored 1-22,30,32-33 Cellulose-Binding Protein Encoded by the sca Gene Cluster of *Ruminococcus flavefaciens*", Journal of Bacteriology, [E-pub] Apr. 27, 2007, vol. 189, No. 13, pp. 4774-4783. See abstract.

Solomon, Kevin V., et al., "Early-branching gut fungi possess a large comprehensive array of biomass-degrading enzymes", Science, [E-Pub] Feb. 18, 2016, vol. 351, No. 6278, pp. 1192-1195. See p. 1192, middle column, second paragraph.

*Primary Examiner* — Albert M Navarro (57) ABSTRACT

Provided herein are novel proteins and protein domains from newly discovered anaerobic fungal species. The anaerobic fungal species have unique enzymatic capabilities, including the ability to digest diverse lignocellulosic biomass feedstocks and to synthesize secondary metabolites. The scope of the invention encompasses novel engineered proteins comprising glycoside hydrolase enzymes, dockerin domains, carbohydrate binding domains, and polyketide synthase enzymes. The invention further encompasses artificial cellulosomes comprising novel proteins and domains of the invention. The scope of the invention further includes novel nucleic acid sequences coding for the engineered proteins of the invention, and methods of using such engineered organisms to degrade lignocellulosic biomass and to create polyketides.

12 Claims, 1 Drawing Sheet

Specification includes a Sequence Listing.

PROTEINS FROM ANAEROBIC FUNGI AND USES THEREOF

CROSS-REFERENCE TO RELATED APPLICATIONS

This application is a continuation application of and claims the benefit of priority to U.S. patent application Ser. No. 15/782,016, entitled "Novel Proteins from Anaerobic Fungi and Uses Thereof," filed Jun. 6, 2018, which is a 35 USC 371 national stage filing of International Patent Application Number PCT/US2016/065579, entitled "Novel Proteins from Anaerobic Fungi and Uses Thereof filed on Dec. 8, 2016, which claims priority to U.S. Provisional Application Ser. No. 62/265,397 entitled "Novel Polyketide Synthase Domains from Fungal Organisms," filed Dec. 9, 2015 and U.S. Provisional Application Ser. No. 62/296,064 entitled "Production of Biofuels from Novel Fungal Strains and Enzymes Derived Therefrom," filed Feb. 16, 2016, the contents of which applications are hereby incorporated by reference in their entirety.

STATEMENT REGARDING FEDERALLY SPONSORED RESEARCH OR DEVELOPMENT

This invention was made with government support under grant number W911NF-09-D-0001 awarded by the United States Army. The government has certain rights in the invention.

REFERENCE TO SEQUENCE LISTING, A TABLE, OR A COMPUTER PROGRAM LISTING COMPACT DISK APPENDIX

The instant application contains a Sequence Listing which has been filed electronically in ASCII format and is hereby incorporated by reference in its entirety. Said ASCII copy, created on Dec. 6, 2016, is named UCSB007PCT_SL.txt and is 21,694,502 bytes in size.

BACKGROUND OF THE INVENTION

Microbial communities have evolved immense enzymatic capabilities. In particular, anaerobic fungi perform metabolic feats which potentially could be adapted for great benefit. For example, the efficient conversion of biomass into fuels could provide humankind with an inexpensive, unlimited, and environmentally sustainable source of energy. However, current biomass conversion technologies are not economically scalable due to the recalcitrance of woody biomass. While humans have struggled to effectively capture energy from biomass, anaerobic fungi efficiently convert such material into many billions of joules of energy each day, in the digestive tracts of herbivores. These organisms have evolved efficient enzymatic machinery to break down cellulosic material in lignin rich plant material.

In addition to efficiently breaking down biomolecules, anaerobic fungi are able to synthesize complex natural products which are difficult or impossible to make using synthetic chemistry. Fungi have rich enzymatic abilities which create a diversity of biologically active molecules. Roughly 40% of drugs in use today were derived from fungi, for example, including antibiotics such as penicillin, chemotherapeutics such as vincristine or vinblastine, and cholesterol-lowering drugs such as statins. The prevalence of useful biomolecules produced by fungi is enabled by their unique enzymatic capabilities.

While the potential of fungi to improve bioproduction technologies is huge, large numbers of fungal species cannot contribute because they are not amenable to culture, isolation, and study. Anaerobic fungi in particular are very difficult to culture compared to model organisms such as aerobic bacteria or yeast. The anaerobic fungi have therefore been severely underrepresented in bioprospecting efforts due to the bottlenecks associated with their study.

Advantageously, the inventors of the present disclosure have developed methodologies for the culture of anaerobic fungi. This development has enable the isolation and characterization of organisms which were never previously studied. From this work, novel species of gut fungi have been isolated and their transcriptomes have been sequenced, revealing a multitude of new genes and proteins that can be used in energy production, in the synthesis of novel compounds, and in other applications.

SUMMARY OF THE INVENTION

The inventors of the present disclosure have identified four novel species of anaerobic fungi and have identified numerous useful protein domains and nucleic acid sequences coding therefor. These novel sequences provide the art with new enzymatic tools. In one aspect, the invention is directed to methods and compositions of matter utilized in the production of biofuels from lignocellulosic biomass utilizing the novel domains of the invention. In one aspect, the scope of the invention encompasses novel catalytic domains applied in the digestion of lignocellulosic biomass. In another aspect, the scope of the invention encompasses structural components which are incorporated into enzyme complexes, such as cellulosomes. Disclosed herein are novel engineered scaffoldins, glycoside hydrolase enzymes, dockerins, cohesins, and domains therefrom, as well as other catalytic proteins and protein domains involved in the breakdown of plant material. In another aspect, the scope of the invention encompasses methods of producing biofuels utilizing the novel organisms described herein in bioreactors or like processes.

In yet another aspect, the scope of the invention encompasses methods and compositions of matter which are utilized in the production of secondary compounds, such as polyketides. In one aspect, the compositions of the invention encompass engineered polyketide synthase complexes comprising one or more novel domains of the invention. In another aspect, the scope of the invention encompasses methods of using the domains of the invention in the production of secondary compounds.

BRIEF DESCRIPTION OF THE DRAWING

FIG. 1 is a conceptual diagram of a cellulosome. The cellulosome complex comprises a scaffoldin (104), comprising a plurality of cohesins (105). Enzymatic moieties comprising catalytic domains (106) are attached to the scaffold by the docking of dockerins (107) to complementary cohesion molecules in dockerin-cohesin complexes (111). The docked proteins further include carbohydrate binding entities (108). The cellulosome is anchored in the cell membrane (103) of a host cell (101) by an anchoring moiety such as a transmembrane helix (102). The cellulosome can digest a complex polymer (109) such as cellulose into monomers (110).

DETAILED DESCRIPTION OF THE INVENTION

Four novel anaerobic gut fungi were isolated and cultured. The organisms include *Piromyces finnis* isolated from horse feces, *Neocallimastix californiae*, isolated from goat feces, *Anaeromyces robustus*, isolated from sheep feces, and *Neocallimastix* sp S4, isolated from sheep feces.

Utilizing novel culture methods, the organisms were isolated and pure cultures were attained, enabling the performance of sequencing efforts. Next-generation sequencing techniques were then utilized identify sequences expressed by the fungal cells. DNA analysis tools were then used to identify domains present in the expressed proteins. By their homology to known sequences, numerous types of useful domains were identified, including catalytic domains and structural domains.

The several domains identified are provided in the sequence listing submitted herewith. Table 1 lists domain names and a description for each domain name which identifies a gene or gene family associated with the sequence, as assigned by bioinformatic tools.

Each domain is represented as a novel polypeptide sequence having a domain description based on its similarity to known proteins from other organisms. Each domain is also provided as a nucleic acid sequence coding for the disclosed polypeptides. The listed protein sequences are provided in standard one-letter amino acid code, as known in the art. The listed nucleic acid sequences comprise fungal cDNA sequences. In the nucleic acids sequence listings, A is adenine; C is cytosine; G is guanine; T is thymine; and N is any of the four bases. The codon preferences of the anaerobic fungi are generally in line with those of model organisms, although fungal sequences tend to have a higher A-T content.

It will be noted that in some cases, multiple variants of a domain are listed, having been derived from the same transcript sequence. This is due to the use of multiple genetic identification tools, which in some cases use diverging models to recognize, define, and annotate protein domains. These models recognize a number of unique features, such as the N- or C-termini of catalytic domains, key catalytic residues, etc, each with their own start and stop sites, resulting in overlapping domain annotations for some transcripts.

The present disclosure provides the art with a large number of novel protein domains and corresponding nucleic acid sequences that may be applied in various contexts. Domains which are applicable to the various compositions and methods described herein can be readily selected from the sequence listing submitted based on the domain labels and descriptions provided in Table 1.

TABLE 1

Domain labels, descriptions, and SEQ ID NO.'s.

| Domain Label | Domain Description | Protein Seq ID No.'s | Nucleic Acid Seq. ID No.'s |
|---|---|---|---|
| (Trans)glycosidases | Glycosidase | 1-155 | 13663-13818 |
| 1-PHOSPHATIDYLINOSITOL PHOSPHODIESTERASE-RELATED PROTEIN | 1-Phosphatidylinositol phosophodiesterase | 156-157 | 13819-13820 |
| 4-PPantetheinyl_Trfase_SF | 4'-phosphopantetheinyl transferase | 158-165 | 13821-13827 |
| 4'-phosphopantetheinyl transferase | 4'-phosphopantetheinyl transferase | 166-173 | 13828-13835 |
| 6-blade_b-propeller_TolB-like | six-bladed beta-propeller domain found in TolB protein | 174 | 13836 |
| 6hp_glycosidase | Glycosidase- six hairpin type | 175-322 | 13837-13984 |
| 9-O-ACETYL-N-ACETYLNEURAMINIC ACID DEACETYLASE-RELATED | 9-O-acetyl-N-acetylneuraminic acid deacetylase | 323-333 | 13885-13995 |
| AAC-RICH MRNA CLONE AAC4 PROTEIN-RELATED | AAC-RICH MRNA CLONE AAC4 PROTEIN-RELATED | 334 | 13996 |
| AB_hydrolase | Alpha-beta hydrolase fold domain found in hydrolytic enzymes | 335-450 | 13997-14112 |
| Abhydrolase_5 | Alpha-beta hydrolase fold domain 5 found in hydrolytic enzymes | 451-464 | 14113-14126 |
| Ac_transferase_dom | Acyl Transferase Domain | 465-578 | 14127-14240 |
| ACCESSORY GLAND PROTEIN ACP76A-RELATED | Accessory Gland Protein domain with similarity to that found in flies | 579-583 | 14241-14245 |
| Acetyl-CoA synthetase-like | Acetyl CoA Synthetase | 584-603 | 14246-14265 |
| ACID PHOSPHATASE RELATED | Acid phosphatase | 604-623 | 14266-14285 |
| ACP DOMAIN | Acyl Carrier Protein | 624-668 | 14286-14330 |
| ACP-like | Acyl Carrier Protein | 669-714 | 14331-14376 |
| ACPS | Acyl Carrier Protein Synthase, a phosphopantetheinyl transferase | 715-722 | 14377-14384 |
| Acyl_carrier_prot-like | Acyl Carrier Protein | 723-767 | 14385-14429 |
| Acyl_transf_1 | Acyl Transferase | 768-798 | 14430-14460 |
| ACYL-COA THIOESTERASE I | Acyl CoA Thioesterase I | 799 | 14461 |
| ADH_N | Catalytic domain of alcohol dehydrogenase | 800-807 | 14462-14469 |
| adh_short | Domain from short chain dehydrogenase family | 808-823 | 14470-14485 |

TABLE 1-continued

Domain labels, descriptions, and SEQ ID NO.'s.

| Domain Label | Domain Description | Protein Seq ID No.'s | Nucleic Acid Seq. ID No.'s |
|---|---|---|---|
| adh_short_C2 | Domain from short chain dehydrogenase C2 family | 824-832 | 14486-14494 |
| ADH_ZINC | Domain from alcohol dehydrogenase, zinc type | 833-835 | 14495-14497 |
| ADH_zinc_N | Domain from alcohol dehydrogenase, zinc type | 836-851 | 14498-14513 |
| ALCOHOL DEHYDROGENASE RELATED | Domain from alcohol dehydrogenase | 852-862 | 14514-14524 |
| Aldolase_TIM | beta/alpha barrel domain found in aldolases | 863-870 | 14525-14532 |
| ALPHA-L-FUCOSIDASE 2 | Alpha-L-fucosidase | 871-874 | 14533-14536 |
| alpha/beta-Hydrolases | Alpha-beta hydrolase fold domain found in hydrolytic enzymes | 875-972 | 14537-14634 |
| Aminotran_1_2 | Class I/Class II Aminotransferase | 973-982 | 14635-14644 |
| AMP BINDING | AMP binding domain | 983-999 | 14645-14661 |
| AMP-binding C | C terminal domain of AMP binding enzyme | 1000-1001 | 14662-14663 |
| Arabinanase/levansucrase/invertase | Member of Arabinanase/levansucrase/invertase superfamily | 1002-1058 | 14664-14720 |
| ARF/SAR SUPERFAMILY PROTEIN-RELATED | Member of small GTPASE superfamily | 1059-1060 | 14721-14722 |
| AT18611P-RELATED | Carbohydrate binding domain | 1061-1062 | 14723-14724 |
| B_KETOACYL_SYNTHASE | Beta-ketoacyl-ACP synthase | 1063-1094 | 14725-14756 |
| Barwin-like endoglucanases | Endoglocanase | 1095-1204 | 14757-14866 |
| Beta_cellobiohydrolase | 1,4-beta cellobiohydrolase | 1205-1286 | 14867-14948 |
| Beta-D-glucan exohydrolase, C-terminal domain | Beta-D-glucan exohydrolase, C-terminal domain | 1287-1297 | 14949-14959 |
| BETA-GALACTOSIDASE | Glycoside hydrolase Beta-Galasctosidase | 1298-1303 | 14960-14965 |
| beta-Galactosidase/glucuronidase domain | beta-Galactosidase/glucuronidase domain | 1304-1309 | 14966-14971 |
| BETA/GAMMA CRYSTALLIN | Beta-Gamma Crystallin Structural Protein | 1310-1316 | 14972-14978 |
| Bgal_small_N | Beta-galactosidase small chain | 1317-1322 | 14979-14984 |
| BNR | BNR repeat sequence | 1323-1324 | 14985-14986 |
| Carb_bind | Carbohydrate Binding Domain | 1325-1327 | 14987-14989 |
| Carbohydrate-binding domain | Carbohydrate Binding Domain | 1328-1333 | 14990-14995 |
| CarboxyPept_regulatory_dom | Regulatory domain of carboxypeptidase | 1334-1337 | 14996-14999 |
| CBD_carb-bd_dom | Carbohydrate Binding Domain | 1338-1344 | 15000-15006 |
| CBD_IV | Cellulose binding domain, Type IV | 1345-1370 | 15007-15032 |
| CBM_1 | Fungal cellulose binding domain | 1371-1419 | 15033-15081 |
| CBM_10 | Dockerin and Carbohydrate Binding Domain, Type 10 | 1420-3705 | 15082-17367 |
| CBM_2 | Carbohydrate Binding Domain, Type 2 | 3706-3709 | 17368-17371 |
| CBM_4_9 | Carbohydrate Binding Domain | 3710-3714 | 17372-17376 |
| CBM_6 | Carbohydrate Binding Domain, family 6 | 3715-3736 | 17377-17398 |
| CBM-like | Carbohydrate Binding Domain | 3737-3740 | 17399-17402 |
| CBM1_1 | Carbohydrate Binding Domain | 3740-3758 | 17403-17420 |
| CBM1_2 | Carbohydrate Binding Domain | 3759-3841 | 17421-17503 |
| CBM6 | Carbohydrate Binding Domain, family 6 | 3842-3850 | 17504-17512 |
| Cellulase | Cellulase | 3851-3962 | 17513-17624 |
| CELLULASE (GLYCOSYL HYDROLASE FAMILY 5) PROTEIN-RELATED | Cellulase- glycosyl hydrolase family 5 | 3963-3972 | 17625-17634 |
| Cellulose docking domain, docketing | Carbohydrate Binding Domain | 3973-6217 | 17635-19879 |
| Cellulose-binding domain | Carbohydrate Binding Domain | 6218-6254 | 19880-19916 |
| CHBHEXC | Chitinase- Chitobiase, C terminal domain | 6255-6262 | 19917-19924 |
| CHIT_BIND_I_1 | Chitin Binding Site, Type 1, may bind N-acetylglucosamine | 6263-6265 | 19923-19927 |
| CHIT_BIND_I_2 | Chitin Binding Site, Type 1, may bind N-acetylglucosamine | 6266-6270 | 19928-19932 |

TABLE 1-continued

Domain labels, descriptions, and SEQ ID NO.'s.

| Domain Label | Domain Description | Protein Seq ID No.'s | Nucleic Acid Seq. ID No.'s |
|---|---|---|---|
| CHITIN DEACETYLASE 1-RELATED | allantoinase/chitin deacetylase 1 | 6271 | 19933 |
| Chitin_bind_1 | Chitin Binding Site, Type 1, may bind N-acetylglucosamine | 6272-6275 | 19934-19937 |
| Chitin-bd_1 | Chitin Binding Site, Type 1, may bind N-acetylglucosamine | 6276-6282 | 19938-19944 |
| CHITINASE | Chitinase | 6283-6291 | 19945-19953 |
| Chitinase insertion domain | Chitinase insertion domain | 6292-6300 | 19954-19962 |
| CHITINASE_18 | Chitinase, family 18 | 6301-6303 | 19963-19965 |
| Chitinase_insertion | Chitinase insertion domain | 6304-6312 | 19966-19974 |
| Chitobiase/Hex_dom_2-like | domain 2 of bacterial chitobiases and beta-hexosaminidases | 6313-6314 | 19975-19976 |
| ChtBD1 | Chitin Binding Site, Type 1, may bind N-acetylglucosamine | 6315-6318 | 19977-19980 |
| CINNAMYL ALCOHOL DEHYDROGENASE 2-RELATED | cinnamyl-alcohol dehydrogenase | 6319-6322 | 19981-19984 |
| ClpP/crotonase | Crotonase like domain | 6323-6333 | 19985-19995 |
| ClpP/crotonase-like_dom | Crotonase like domain | 6334-6344 | 19996-20006 |
| CoA-dependent acyltransferases | CoA-dependent acyltransferases | 6345-6349 | 20007-20011 |
| ConA-like_subgrp | Concanavalin A-like lectins/glucanases | 6350-6375 | 20012-20037 |
| Concanavalin A-like lectins/glucanases | Concanavalin A-like lectins/glucanases | 6376-6433 | 20038-20095 |
| Condensation | Condensation domain | 6434-6436 | 20096-20098 |
| CotH | spore coat protein, involved in plant cell wall binding | 6437-6584 | 20099-20246 |
| Cystine-knot_cytokine | Cystine-knotcytokine | 6585 | 20247 |
| CYTH-like phosphatases | Phosphatase- acts on triphosphorylated substrates | 6586-6587 | 20248-20249 |
| CYTH-like_domain | Phosphatase- acts on triphosphorylated substrates | 6588-6589 | 20250-20251 |
| Dockerin_dom | Dockerin domain | 6590-7679 | 20252-21341 |
| Dockerin_dom_fun | Dockerin domain | 7680-8910 | 21342-22572 |
| DPBB_1 | Lytic transglycolase | 8911-8919 | 22573-22581 |
| DUF1729 | Domain of unknown function- Found in acyl transferase domains | 8920-8930 | 22582-22592 |
| DUF303 | Domain of unknown function DUF303, acetylesterase | 8931-8946 | 22593-22608 |
| DUF4353 | Domain of unknown function | 8947-8949 | 22609-22611 |
| ECH | Enoyl-CoA hydratase | 8950-8959 | 22612-22621 |
| EGGSHELL | eggshell | 8960-8963 | 22622-22625 |
| Endo-1-4-beta-glucanase_dom2 | Endo-1-4-beta-glucanase, domain 2 | 8964 | 22626 |
| ENDO-1,4-BETA-GLUCANASE | Endo-1-4-beta-glucanase | 8965-8998 | 22627-22660 |
| ENDOGLUCANASE | Endoglucanse | 8999-9022 | 22661-22684 |
| Endoglucanase_F_dom3 | Endoglucase F, domain 3 | 9023-9055 | 22685-22717 |
| ENTEROBACTIN SYNTHASE COMPONENT F | Entorbactin Synthase Component F | 9056 | 22718 |
| Esterase | Esterase | 9057-9080 | 22719-22742 |
| Expansin_CBD | C-terminal carbohydrate binding domain of expansin | 9081-9106 | 22743-22768 |
| EXPANSIN_EG45 | N terminal domain of expansin | 9107-9127 | 22769-22789 |
| EXTRACELLULAR MATRIX GLYCOPROTEIN RELATED | Extracellular matrix glycoprotein related domain | 9128-9129 | 22790-22791 |
| FabD/lysophospholipase-like | FabD/lysophospholipase-like domain- found in hydrolases | 9130-9240 | 22792-22902 |
| FAMILY NOT NAMED | Not associated with known sequences | 9240-9338 | 22903-23600 |
| FASYNTHASE | Fatty Acid Synthase | 9339-9468 | 23601-23130 |
| FATTY ACID SYNTHASE SUBUNIT BETA | Fatty Acid Synthase- subunit beta | 9469-9479 | 23131-23141 |
| fCBD | Cellulose binding domain | 9480-9605 | 23142-23267 |
| fn3_3 | domain II of rhamnogalacturonan lyase | 9606-9609 | 23268-23271 |
| Fn3_assoc | domain II of rhamnogalacturonan lyase | 9610 | 23272 |
| Fn3-like | domain II of rhamnogalacturonan lyase | 9611-9619 | 23273-23281 |

TABLE 1-continued

Domain labels, descriptions, and SEQ ID NO.'s.

| Domain Label | Domain Description | Protein Seq ID No.'s | Nucleic Acid Seq. ID No.'s |
|---|---|---|---|
| Galactose mutarotase-like | Galactose mutarotase-like domain- binds carbohydrates | 9620-9626 | 23282-23288 |
| Galactose-bd-like | Galactose binding domain-like fold | 9627-9668 | 23289-23330 |
| Galactose-binding domain-like | Galactose binding domain-like fold | 9669-9727 | 23331-23389 |
| GDHRDH | short-chain dehydrogenases/reductase family | 9728-9748 | 23390-23410 |
| GH_fam_N_dom | domain is found towards the N terminus of some glycosyl hydrolase family members, including alpha-L-fucosidases | 9749-9753 | 23411-23415 |
| GH04125P-RELATED | Serine protease inhibitor related | 9754 | 23416 |
| GH97_C | Glycosyl-hydrolase 97, C-terminal oligomerisation domain | 9755 | 23417 |
| GH97_N | Glycosyl-hydrolase 97, N-terminal domain | 9756 | 23418 |
| GLHYDRLASE10 | Glycoside hydrolase family 10 domain | 9757-9889 | 23419-23551 |
| GLHYDRLASE11 | Glycoside hydrolase family 11 | 9890-9998 | 23552-23660 |
| GLHYDRLASE16 | Glycoside hydrolase family 16 | 9999-10013 | 23661-23675 |
| GLHYDRLASE2 | Glycoside hydrolase family 2 | 10014-10028 | 23676-23690 |
| GLHYDRLASE26 | Glycoside hydrolase family 26 | 10029-10054 | 23691-23716 |
| GLHYDRLASE3 | Glycoside hydrolase, family 3, N-terminal | 10055-10094 | 23717-23756 |
| GLHYDRLASE48 | Glycoside hydrolase family 48 | 10095-10308 | 23757-23970 |
| GLHYDRLASE6 | Glycoside hydrolase family 6 | 10309-10791 | 23971-24453 |
| GLHYDRLASE8 | Glycoside hydrolase family 8 | 10792-10818 | 24454-24480 |
| GLUCOSE-METHANOL-CHOLINE (GMC) OXIDOREDUCTASE | Glucose-methanol-choline oxidoreductase | 10819-10820 | 24481-24482 |
| GLUCOSYLCERAMIDASE | Glucosylceramidase | 10821-10823 | 24483-24485 |
| Glyco_10 | Glycoside hydrolase family 10 | 10824-10858 | 24486-24520 |
| Glyco_18 | Glycoside hydrolase family 18 | 10859-10865 | 24521-24527 |
| Glyco_hyd_65N_2 | N-terminus of the glycosyl hydrolase 65 family catalytic domain | 10866-10870 | 24528-24532 |
| Glyco_hydr_30_2 | Glycoside hydrolase family 30 | 10871-10873 | 24533-24535 |
| Glyco_hydro_10 | Glycoside hydrolase family 10 | 10874-10913 | 24536-24575 |
| Glyco_hydro_11 | Glycoside hydrolase family 11 | 10914-10949 | 24576-24611 |
| Glyco_hydro_11/12 | Glycoside hydrolase family 11/12 | 10950-10986 | 24612-24684 |
| Glyco_hydro_114 | Glycosyl-hydrolase family, number 114potential endo-alpha-1,4-polygalactosaminidase | 10987-10989 | 24685-24651 |
| Glyco_hydro_13_b | Glycoside hydrolase family 13 | 10990-10991 | 24652-24653 |
| Glyco_hydro_16 | Glycoside hydrolase family 16 | 10992-11001 | 24654-24663 |
| Glyco_hydrol_8 | Glycoside hydrolase family 18 | 11002-11010 | 24664-24672 |
| Glyco_hydro_2 | Glycoside hydrolase family 2 | 11011-11013 | 24673-24675 |
| Glyco_hydro_2_C | Glycoside hydrolase family 2 | 11014-11016 | 24676-24678 |
| Glyco_hydro_2_N | Glycoside hydrolase family 2- N terminal domain | 11017-11019 | 24679-24681 |
| Glyco_hydro_2/20_Ig-like | Glycoside hydrolase, family 2/20, immunoglobulin-like beta-sandwich domain | 11020-11025 | 24682-24687 |
| Glyco_hydro_26 | Glycoside hydrolase family 26 | 11026-11032 | 24688-24694 |
| Glyco_hydro_3 | Glycoside hydrolase family 3 | 11033-11041 | 24695-24703 |
| Glyco_hydro_3_C | Glycoside hydrolase family 3- C terminal domain | 11042-11059 | 24704-24721 |
| Glyco_hydro_3_N | Glycoside hydrolase family 3 - N terminal domain | 11060-11068 | 24722-24730 |
| Glyco_hydro_39 | Glycoside hydrolase family 39 | 11069-11081 | 24731-24743 |
| Glyco_hydro_43 | Glycoside hydrolase family 43 | 11082-11129 | 24744-24791 |
| Glyco_hydro_45 | Glycoside hydrolase family 45 | 11130-11153 | 24792-24815 |
| Glyco_hydro_48 | Glycoside hydrolase family 48 | 11154-11186 | 24816-24848 |
| Glyco_hydro_53 | Glycoside hydrolase family 53 | 11187-11189 | 24849-24851 |
| Glyco_hydro_6 | Glycoside hydrolase family 6 | 11190-11270 | 24852-24932 |
| Glyco_hydro_8 | Glycoside hydrolase family 8 | 11271-11276 | 24933-24938 |
| Glyco_hydro_88 | Glycoside hydrolase family 88 | 11277-11278 | 24939-24940 |
| Glyco_hydro_9 | Glycoside hydrolase family 9 | 11279-11312 | 24941-24974 |
| Glyco_hydro_97 | Glycoside hydrolase family 97 | 11313 | 24975 |
| Glyco_hydro_beta-prop | five-bladed beta-propellor domain found in some glycosyl hydrolases | 11314-11361 | 24976-25023 |

TABLE 1-continued

Domain labels, descriptions, and SEQ ID NO.'s.

| Domain Label | Domain Description | Protein Seq ID No.'s | Nucleic Acid Seq. ID No.'s |
|---|---|---|---|
| Glyco_hydro_catalytic_dom | catalytic TIM beta/alpha barrel common to many different families of glycosyl hydrolases | 11362-11510 | 25024-25172 |
| Glyco_hydro-type_carb-bd_sub | Carbohydrate binding domain from glycoside hydrolases | 11511-11517 | 25173-25179 |
| Glycoside hydrolase/deacetylase | Glycoside hydrolase/deacetylase family | 11518-11521 | 25180-25183 |
| GLYCOSYL HYDROLASE 43 FAMILY MEMBER | Glycoside hydrolase family 43 | 11522-11560 | 25184-25222 |
| Glycosyl hydrolase domain | catalytic TIM beta/alpha barrel common to many different families of glycosyl hydrolases | 11561-11562 | 25223-25224 |
| GLYCOSYL HYDROLASE-RELATED | related to known glycosyl hydrolase domains | 11563-11564 | 25225-25226 |
| Glycosyl hydrolases family 6, cellulases | Glycosyl hydrolases family 6, cellulases | 11565-11648 | 25227-25310 |
| GLYCOSYL TRANSFERASE-RELATED | Glycosyl transferase related domain | 11649-11669 | 25311-25331 |
| GLYCOSYL_HYDROL_F10 | Glycoside hydrolase family 10 | 11670-11688 | 25332-25350 |
| GLYCOSYL_HYDROL_F11_1 | Glycoside hydrolase family 11 | 11689-11719 | 25351-25381 |
| GLYCOSYL_HYDROL_F11_2 | Glycoside hydrolase family 11 | 11720-11721 | 25382-25383 |
| GLYCOSYL_HYDROL_F3 | Glycoside hydrolase family 3 | 11722 | 25384 |
| GLYCOSYL_HYDROL_F45 | Glycoside hydrolase family 45 | 11723-11742 | 25385-25404 |
| GLYCOSYL_HYDROL_F5 | Glycoside hydrolase family 5 | 11743-11765 | 25405-25427 |
| GLYCOSYL_HYDROL_F6_2 | Glycoside hydrolase family 6 | 11766-11816 | 25428-25478 |
| GLYCOSYL_HYDROL_F9_2 | Glycoside hydrolase family 9-signature found in endglucanases and other glycoside hydrolases | 11817-11844 | 25479-25506 |
| GroES-like | Similarity to GroES (chaperonin 10), an oligomeric molecular chaperone | 11845-11882 | 25507-25544 |
| HMG_CoA_synt_C | Hydroxymethylglutaryl-coenzyme A synthase C-terminal domain | 11883-11888 | 245545-25550 |
| HMG_CoA_synt_N | Hydroxymethylglutaryl-coenzyme A synthase N-terminal domain | 11889-11891 | 25551-25553 |
| HotDog_dom | domain found in thioesterases and thiol ester dehydratase-isomerases | 11892-11921 | 25554-25583 |
| HxxPF_rpt | HxxPF-repeat domain. This family is found in non-ribosomal peptide synthetase proteins. | 11922 | 25584 |
| ICP-like | ICP-like domain | 11923 | 25585 |
| Inhibitor_I42 | Protease inhibitor | 11924 | 25586 |
| Inosine monophosphate dehydrogenase (IMPDH) | Inosine monophosphate dehydrogenase | 11925-11933 | 25587-25595 |
| Integrin alpha N-terminal domain | Integrin alpha N-terminal domain | 11934-11937 | 25596-25599 |
| KAZAL_1 | serine proteinase inhibitor | 11938 | 25600 |
| ketoacyl-synt | Beta-ketoacyl synthase | 11939-11983 | 25601-25645 |
| Ketoacyl-synt_C | Beta-ketoacyl synthase, C-terminal domain | 11984-12027 | 25646-25689 |
| KR | Ketoreductase | 12028-12043 | 25690-25705 |
| L domain-like | Leucine rich repeat domain | 12044-12047 | 25706-25709 |
| LamGL | LamG-like jellyroll fold | 12048-12050 | 25710-25712 |
| Laminin_G_3 | This domain belongs to the Concanavalin A-like lectin/glucanases superfamily | 12051-12053 | 25713-25715 |
| LEUCINE-RICH REPEAT RECEPTOR-LIKE PROTEIN KINASE | Leucine-Rich Repeat Receptor-Like Kinase1 | 12054-12057 | 25716-25719 |
| Lipase_GDSL | Domain from GDSL esterases and lipases | 12058-12067 | 25720-25729 |
| Lipase_GDSL_2 | Domain from family of presumed lipases and related enzymes | 12068-12070 | 25730-25732 |
| LRR | Leucine rich repeat | 12071-12082 | 25733-25744 |
| LRR_1 | Leucine rich repeat | 12083-12090 | 25745-25752 |
| LRR_4 | Leucine rich repeat | 12091-12093 | 25753-25755 |
| LRR_6 | Leucine rich repeat | 12094 | 25756 |
| LRR_8 | Leucine rich repeat | 12095-12098 | 25757-25760 |
| LRR_SD22 | Leucine rich repeat | 12099-12101 | 25761-25763 |

TABLE 1-continued

Domain labels, descriptions, and SEQ ID NO.'s.

| Domain Label | Domain Description | Protein Seq ID No.'s | Nucleic Acid Seq. ID No.'s |
|---|---|---|---|
| LRR_TYP | Leucine rich repeat- typical subtype | 12102-12116 | 25764-25778 |
| LYSOPHOSPHOLIPASE-RELATED | Lysophospholipase related domain | 12117 | 25779 |
| MALONYL COA-ACYL CARRIER PROTEIN TRANSACYLASE | Malonyl-CoA:acyl carrier protein transacylase | 12118-12128 | 25780-25790 |
| MaoC_dehydrat_N | N-terminal domain of MaoC dehydratase | 12129-12137 | 25791-25799 |
| MaoC_dehydratas | C-terminal doamin of MaoC dehydratase | 12138-12152 | 257800-25814 |
| Metallo-dependent phosphatases | Metallo-dependent phosphatases | 12153-12202 | 25815-25864 |
| Metallo-depent_PP-like | Metallo-dependent phosphatases | 12203-12245 | 25865-25907 |
| Metallophos | Metallo-dependent phosphatases | 12246-12281 | 25908-25943 |
| Mucin | Mucins, high molecular weight glycoconjugates | 12282-12283 | 25944-25945 |
| NAD(P)-bd_dom | NADP binding domain | 12284-12334 | 25946-25996 |
| NAD(P)-binding Rossmann-fold domains | NAD(P)-binding Rossmann-fold domains | 12335-12384 | 25997-26046 |
| NODB | catalytic domain found in members of carbohydrate esterase family 4 | 12385 | 26047 |
| Oligoxyloglucan reducing end-specific cellobiohydrolase | Oligoxyloglucan reducing end-specific cellobiohydrolase | 12386-12397 | 26048-26059 |
| Pectin lyase-like | Pectin-lyase like domain | 12398-12408 | 26060-26070 |
| Pectin_lyas_fold | Pectin lyase fold domain | 12409-12417 | 26071-26079 |
| Peptidase_S8 | Peptidase_S8 | 12418-12421 | 26080-26083 |
| Peptidase_S8/S53_dom | domain found in serine peptidases | 12422-12427 | 26084-26089 |
| PERIPLASMIC BETA-GLUCOSIDASE-RELATED | Periplasmic Beta-glucosidase related domain | 12428-12437 | 26090-26099 |
| PERIPLASMIC BROAD-SPECIFICITY ESTERASE/LIPASE/PROTEASE | Periplasmic broad specificity esterase/lipase/protease | 12438-12441 | 26100-26103 |
| PEROXISOMAL MULTIFUNCTIONAL ENZYME TYPE 2 | Peroxisomal multifunctional enzyme type 2 | 12442-12445 | 2614-26107 |
| PHL pollen allergen | PHL pollen allergen | 12446-12462 | 26108-26124 |
| PHOSPHOPANTETHEINE | Prosthetic group of acyl carrier protein | 12463-12473 | 26125-26135 |
| PI-PLC-X | PI-PLC X domain | 12474 12475 | 26136-26137 |
| PIPLC_X_DOMAIN | PI-PLC X domain | 12476-12478 | 26138-26140 |
| PKS_AT | Acyl Transferase domain | 12479-12509 | 26141-26171 |
| PKS_ER | Enoyl Reductase | 12510-12525 | 26172-26178 |
| PKS_KR | Ketoreductase | 12526-12545 | 26179-26198 |
| PKS_KS | Ketosynthase | 12546-12579 | 26199-26241 |
| PKS_PP | phosphopantetheine-binding domain | 12580-12607 | 26242-26269 |
| Plant lectins/antimicrobial peptides | Plant lectins/antimicrobial peptides | 12608-12612 | 26270-26274 |
| PLC-like phosphodiesterases | PLC-like phosphodiesterases | 12613-12618 | 26275-26280 |
| PLC-like_Pdiesterase_TIM-brl | domain consisting of a TIM beta/alpha-barrel, found in several phospholipase C like phosphodiesterases | 12619-12622 | 26281-26284 |
| PLCXc | Phosphatidylinositol-specific phospholipase C, X domain | 12623-12624 | 26285-26286 |
| PLP-dependent transferases | PLP-dependent transferases | 12625-12634 | 26287-26296 |
| POLYKETIDE SYNTHASE-RELATED | Related to sequences found in PKS domains | 12635-12679 | 26297-26314 |
| Polysac_deacetylase | Polysaccharide deacetylase | 12680-12683 | 26314-26345 |
| Polysacc_deac_1 | domain found in polysaccharide deacetylase | 12684-12687 | 26346-26349 |
| PP-binding | phosphopantetheine-binding domain | 12688-12727 | 26350-26389 |
| Probable ACP-binding domain of malonyl-CoA ACP transacylase | Probable ACP-binding domain of malonyl-CoA ACP transacylase | 12728-12740 | 26390-26402 |

TABLE 1-continued

Domain labels, descriptions, and SEQ ID NO.'s.

| Domain Label | Domain Description | Protein Seq ID No.'s | Nucleic Acid Seq. ID No.'s |
|---|---|---|---|
| PROKAR_LIPOPROTEIN | Prokaryotic lipoprotein domain | 12741-12761 | 26403-26423 |
| PROPROTEIN CONVERTASE SUBTILISIN/KEXIN | Proprotein convertase subtilisin/kexin type 9 | 12762-12764 | 26424-26426 |
| PROSTAGLANDIN REDUCTASE 1 | Prostaglandin reductase 1 domain | 12765-12767 | 26427-26429 |
| PROTEIN C41A3.1 | Protein C41A3.1 | 12768-12770 | 26430-26432 |
| PS-DH | Polyketide synthase, dehydratase domain | 12771-12785 | 26433-26447 |
| PT | Polyketide product template domain | 12786-12787 | 26448-26449 |
| PURPLE ACID PHOSPHATASE 23 | purple acid phosphatase 23 | 12788-12797 | 26450-26459 |
| Purple acid phosphatase, N-terminal domain | Purple acid phosphatase, N-terminal domain | 12898-12829 | 26460-26491 |
| Purple_acid_Pase_N | Purple acid phosphatase, N-terminal domain | 12830-12861 | 26492-26523 |
| PyrdxlP-dep_Trfase_major_sub1 | Pyridoxal phosphate-dependent transferase, major region, subdomain 1 | 12862-12871 | 26524-26533 |
| PyrdxlP-dep_Trfase_major_sub2 | Pyridoxal phosphate-dependent transferase, major region, subdomain 2 | 12872-12879 | 26534-26541 |
| Rhamnogal_lyase | Rhamnogalacturonate lyase | 12880-12883 | 26542-26545 |
| RhgB_N | Rhamnogalacturonase B, N-terminal domain | 12884-12885 | 26546-26547 |
| RICIN | Ricin | 12886-12950 | 26548-26612 |
| Ricin B-like lectins | Ricin B-like lectins | 12951-13037 | 26613-26699 |
| RICIN_B_LECTIN | Ricin B-like lectins | 13038-13108 | 26699-26770 |
| RicinB_lectin_2 | Ricin B-like lectins | 13109-13186 | 26771-26848 |
| SCP-like | Spore coat protein like domain | 13187-13189 | 26849-26851 |
| SCP2 | Spore coat protein 2 | 13190-13192 | 26852-26854 |
| SCP2_sterol-bd_dom | SCP2 sterol-binding domain | 13193-13195 | 26855-26857 |
| SDRFAMILY | Short-chain dehydrogenase/reductase | 13196-13207 | 26858-26869 |
| SERINE PROTEASE INHIBITOR, SERPIN | Serine protease inhibitor | 13208-13215 | 26870-26877 |
| SERINE/THREONINE PROTEIN KINASE | Serine/threonine protein kinase | 13216 | 26878-26878 |
| SERPIN | Serine protease inhibitor | 13217-13242 | 26879-26904 |
| Serpins | Serine protease inhibitor | 13243-13253 | 26905-26915 |
| SGNH hydrolase | SGNH hydrolase domain | 13252-13294 | 26916-26956 |
| SGNH_hydro-type_esterase_dom | SGNHhydro-type esterase domain | 13295-13307 | 26957-26969 |
| Six-hairpin glycosidases | six-hairpin glycoside domain | 13308-13389 | 26970-27051 |
| Starch-binding domain-like | Starch-binding domain-like | 13392-13393 | 27052-27055 |
| SUBTILASE_ASP | Serine proteases, subtilase family, aspartic acid active site | 13394-13395 | 27056-27057 |
| SUBTILASE_HIS | Serine proteases, subtilase family, histidine active site. | 13396-13397 | 27058-27059 |
| SUBTILASE_SER | Serine proteases, subtilase family, serine active site. | 13398-13399 | 27060-27061 |
| SUBTILISIN | Protease domain | 13400-13407 | 27062-27069 |
| Subtilisin-like | Subtilisin-like protease domain | 13408-13416 | 27070-27078 |
| Thioesterase | Thioesterase | 13417-13419 | 27079-27081 |
| Thioesterase/thiol ester dehydrase-isomerase | Thioesterase/thiol ester dehydrase-isomerase | 13420-13449 | 27082-27111 |
| Thiolase-like | Thiolase-like domain | 13450-13544 | 27112-27206 |
| Thiolase-like_subgr | Thiolase-like_subgr | 13545-13637 | 27207-27299 |
| Thioredoxin-like | Thioredoxin-like | 13638 | 27300 |
| Thioredoxin-like_fold | Thioredoxin-like fold domain | 13639 | 27301 |
| TIGR00556 | phosphopantetheine--protein transferase domain | 13640-13647 | 27302-27309 |
| TIGR01733 | amino acid adenylation domain | 13648 | 27310 |
| TIGR01833 | hydroxymethylglutaryl-CoA synthase | 13649-13650 | 27311-27312 |
| TRANS-2-ENOYL-COA REDUCTASE, MITOCHONDRIAL | Enoyl- CoA reductase | 13651-13654 | 27313-27316 |

TABLE 1-continued

Domain labels, descriptions, and SEQ ID NO.'s.

| Domain Label | Domain Description | Protein Seq ID No.'s | Nucleic Acid Seq. ID No.'s |
|---|---|---|---|
| UNCHARACTERIZED VCBS | Uncharacterized VCBS repeat domain | 13655-13656 13657 | 27317-27318 27319 |
| ZINC FINGER FYVE DOMAIN CONTAINING PROTEIN | Zinc finger FYVE domain-containing protein | 13658-13659 | 27320-27321 |
| ZINC FINGER-CONTAINING PROTEIN | Zinc finger containing protein | 13660-13662 | 27322-27324 |

Engineered Proteins

The domains disclosed herein may be utilized in the creation of "engineered proteins." As used herein, a "protein of the invention," or an "engineered protein" will refer to a non-naturally occurring protein, wherein such protein comprises one or more domains selected from SEQ. ID NO: 1-13662. A non-naturally occurring protein means the protein is not found in any wild-type species, having been engineered by molecular biological techniques known in the art. For example, the engineered protein may comprise heterologous elements, i.e. elements from different species. Alternatively, the engineered protein may comprise an anaerobic fungal protein lacking heterologous elements, but wherein the elements of the protein have been modified in some way such that they differ from those of the native protein, for example by rearrangement, duplication, or deletion of elements.

The domains disclosed herein will impart various properties to the engineered proteins in which they are incorporated. In some cases, the domain will comprise a structural element and will impart a structural property to the engineered protein. In another embodiment, the domain will comprise a binding domain and will impart a binding affinity for specific binding partners. In other embodiments, the domain will comprise a catalytic domain and will impart an enzymatic activity to the engineered protein.

The various domains of SEQ ID NO: 1-13662 encompass a wide variety of domains having diverse properties. One of skill in the art may readily select a domain of the invention for incorporation into an engineered protein based on the putative functions assigned to the domain. The putative functions of various domains of SEQ ID NO: 1-13662 are listed as "domain descriptions" in Table 1. Methods of using the engineered proteins of the invention will be readily ascertained by the skilled practitioner based upon the properties of the one or more domains of SEQ ID NO: 1-13662 and any additional properties imparted by accessory elements in the engineered proteins.

The proteins of the invention may include chemically synthesized polypeptides and recombinantly produced polypeptides comprising the domain sequences disclosed herein. The scope of the invention will be understood to extend to derivatives of the disclosed domain sequences. The term "derivative," as used herein with reference to the polypeptides of the invention refers to various modifications, analogs, and products based on the polypeptide sequences disclosed herein, as described below.

Protein derivatives of the invention include substantial equivalents of the disclosed amino acid sequences, for example polypeptides having at least 65%, at least 70%, at least 75%, at least 80%, at least 85%, at least 90%, at least 95%, or at least 99% amino acid sequence identity to a disclosed domain and/or which retain the biological activity of the unmodified sequences.

Protein derivatives of the invention further include polypeptides disclosed herein which have been modified by such techniques as ubiquitination, labeling (e.g., with radioactive or fluorescent moieties), covalent polymer attachment, etc. Derivative proteins of the invention include post-translational modifications of the polypeptide including, but not limited to, acetylation, carboxylation, glycosylation, phosphorylation, lipidation and acylation, etc.

Proteins derivatives of the invention further include polypeptides differing from the sequences disclosed herein by amino acid substitutions. For example, amino acid substitutions that largely preserve the secondary or tertiary structure of the original polypeptide may be selected on the basis of similarity in polarity, charge, solubility, hydrophobicity, hydrophilicity, and/or the amphipathic properties of specific residues. Determination of which amino acid substitutions may be made while maintaining enzymatic and other activities of interest is within ability of one of ordinary skill in the art of protein engineering. The invention also comprises substitutions with non-naturally occurring amino acids, amino acid analogs, etc.

Proteins derivatives of the invention further include mutations in the disclosed polynucleotide sequence intentionally introduced to enhance or modify characteristics of the polypeptide, such as to alter post-translational processing, binding affinities (e.g. introduction of specific epitopes for antibody binding), degradation/turnover rate, industrial processing compatibility (e.g. optimized expression, purification, etc.) or other properties.

The invention further comprises truncated versions of the protein domains disclosed herein, for example C-terminal, N-terminal, or internal deletions encompassing, for example, 1-20 amino acids. The invention further comprises isolated functional units from the disclosed domain sequences, for example isolated binding domains, catalytic domains, and other motifs having useful structures or functions which may be used in isolation from the remainder of the protein.

The invention further comprises any of the disclosed polypeptides sequences which have been augmented with additional amino acids. For example, the invention also includes fusion proteins and chimeric proteins in which a disclosed polypeptide sequences or sub-sequences thereof is combined with other peptides, proteins, or amino acid sequences. Exemplary fusion or chimeric proteins include the disclosed domain polypeptide sequences, or sub-sequences thereof, which have been combined with functional sequences from different proteins. Such proteins may further include secondary polypeptide sequences that impart desired properties such as enhanced secretion, or which enable purification (e.g. His-Tags), immobilization, and other desirable properties.

The invention further includes antibodies that specifically recognize one or more epitopes present on the disclosed polypeptides, as well as hybridomas producing such antibodies.

Polynucleotide Constructs

The scope of the invention further encompasses any nucleic acid construct which codes for an engineered protein of the invention or codes for an engineered multiple enzyme complex of the invention. For example, the nucleic acid constructs of the invention may include any non-naturally occurring nucleic acid construct which comprises one or more nucleic sequences selected from SEQ ID NO: 13362-27324 or SEQ ID NO: 27328-27330, (corresponding to the proteins of SEQ ID NO: 1-13662 and SEQ ID NO: 27325-27327). However, it will be understood that, due to the redundancy of the genetic code and the diverging codon preferences in different species, that nucleic acid sequences coding for the proteins of SEQ ID NO: 1-13662 and SEQ ID NO: 27325-27327 are not limited to the fungal derived sequences disclosed in SEQ ID NO: 13663-27324 and SEQ ID NO: 27328-27330, and may comprise any nucleic acid construct comprising a sequence coding for the selected domain.

The polynucleotide sequences of the invention encompass DNA, RNA, DNA-RNA hybrids, peptide nucleic acid (PNA) or any other DNA-like or RNA-like material. For clarity, the polynucleotide sequences disclosed herein do not encompass genomic DNA sequences as present in their natural source (e.g. native organism). The polynucleotide sequences of the invention do not contain introns or untranslated 3-prime and 5-prime sequences. The polynucleotide sequences encompass translated sequences only.

The nucleic acid constructs of the invention encompass sequences which are the reverse or direct complement of any of the disclosed nucleic acid sequences (or their derivatives, as described below). Polynucleotide constructs of the invention may comprise single-stranded or double-stranded polynucleotides and may represent the sense or the antisense strand. The nucleic acid constructs of the present invention also include nucleic acid sequences that hybridize to the disclosed nucleotide sequences or their complements under stringent conditions. Polynucleotide constructs of the invention include sequences having high sequence similarity to the disclosed sequences (and their derivatives), for example, sequences having at least 80% homology, at least 85% homology, at least 90% homology, at least 95% homology, or at least 99% homology.

The polynucleotide constructs of the invention further encompass constructs comprising sequences which are derivatives of the disclosed domain polynucleotide sequences. As used herein, with reference to domain polynucleotide sequences, the term "derivative" refers to complementary sequences, degenerate sequences, truncated or augmented sequences, modified sequences, and other polynucleotides based upon the disclosed sequences. One form of polynucleotide derivative contemplated within the scope of the invention is a polynucleotide comprising nucleotide substitutions. For example, utilizing the redundancy in the genetic code, various substitutions may be made within a given polynucleotide sequence that result in a codon which codes for the identical amino acid as coded for in the original sequence, and which such change does not alter the composition of the polypeptide coded by a polynucleotide. Such "silent" substitutions may be selected by one of skill in the art. Likewise, nucleotide substitutions are contemplated which result in an amino acid substitution, wherein the amino acid is of similar polarity, charge, size, aromaticity, etc., such that the resulting polypeptide is of identical or substantially similar structure and function as a polypeptide resulting from an unmodified sequence. Further, the invention also comprises nucleotide substitutions which result in amino acid substitutions which create a polypeptide derivative, as described above.

It is also understood by one of skill in the art that various nucleotide analogs, modified nucleotides, and other compositions may be substituted for the nucleotides of the disclosed DNA sequences and their derivatives, for example modified or non-naturally occurring nucleotides such as 5-propynyl pyrimidines (i.e., 5-propynyl-dTTP and 5-propynyl-dTCP), 7-deaza purines (i.e., 7-deaza-dATP and 7-deaza-dGTP). Nucleotide analogs include base analogs and comprise modified forms of deoxyribonucleotides as well as ribonucleotides.

Additionally, substitutions in a disclosed polynucleotide sequence may be made which enable the translation of polypeptides from the polynucleotide sequence within a specific expression system. For example, as the polynucleotides of the invention are isolated from fungal species, it is contemplated that the disclosed sequences may be modified as necessary to enable or optimize expression of proteins in eukaryotic, yeast, insect, plant, mammalian, or in other expression systems such as cell-free and chemical systems. The selection of proper substitutions for proper expression within a given expression system is within the skill of one in the art of molecular biology.

Polynucleotide derivatives of the invention also comprise augmented or chimeric sequences, wherein a disclosed polynucleotide sequence has been modified to include additional nucleotides. For example, a disclosed polynucleotide sequence, or subsequences thereof, may be ligated with additional polypeptide sequences which enhance expression (for example, promoter sequences), or which alter the properties of the resulting polypeptide, such as sequences which enhance secretion, enable isolation (e.g. sequences which code for His-Tags or like moieties), enable immobilization, or other useful sequences as known in the art.

The scope of the invention additionally includes vectors, comprising the polynucleotide constructs of the invention integrated into vectors. Exemplary vectors include plasmids, phages, and viral constructs which promote efficient maintenance, amplification, and transcription of the polynucleotide sequences in an expression system. The nucleic acid constructs may comprise sequences integrated into the genome of an organism by transduction techniques known in the art.

Engineered Organisms

In one aspect, the scope of the invention encompasses organisms which have been genetically engineered to express one or more engineered protein of the invention, i.e. proteins comprising the protein domains selected from SEQ. ID NO: 1-13662. The engineered organisms of the invention further encompass organisms which express any of the ScaA full proteins of SEQ ID NO: 27325-27327, or portions thereof. Likewise, engineered organisms may comprise the nucleic acid constructs of the invention, for example, with the nucleic acid sequences being transiently expressed by the organism or being stably integrated into the genome of the organism. In one implementation of the invention, the engineered organism is an organism expressing one or more of nucleic acid sequences selected from SEQ ID NO: 13663-27324 or SEQ ID NO: 27328-27330.

Engineered organisms of the invention may comprise any species, for example, fungal species, yeast, bacteria, plants, and other organisms genetically modified to produce one or more engineered proteins of the invention. The engineered organisms of the invention may further comprise cell lines, such as insect cell cultures, CHO cells, and other cell culture systems used in the production of recombinant proteins.

Engineered Enzymes for Bioprocessing

The various inventions described herein may be applied in numerous bioprocessing methods. The present description is largely directed to bioprocessing methods for the digestion of lignocellulosic biomass into fermentable monomers. However, it will be understood that the engineered proteins and organisms described herein may be applied in other bioprocessing methods, for example, for the synthesis of chemicals from feedstocks, including polymers, biofuels, and others.

In one aspect, the engineered proteins of the invention encompass proteins which participate in the breakdown of lignocellulosic biomass. In one embodiment, the engineered proteins of the invention comprise a glycoside hydrolase or other enzyme capable of digesting a component of lignocellulosic materials. For example, the engineered enzyme of the invention may comprise a cellulase, glycosidase, esterase, SGNH hydrolase, endoglucanase, cellobiohydrolase, Beta-D-glucan exohydrolase, beta-glucanase, phosphatidylinositol phosphodiesterase, pectin lyase, fucosidase, glycoside hydrolase, glycosyl hydrolase, hemicellulsase, xyanlase, galactosaminoglycan glycanohydrolase, amylase, chitinase, β-glucuronyl hydrolase, trehalase, glucoamylase, β-glucuronyl hydrolase, or acid phosphatase. In one embodiment, the engineered protein of the invention is a glycoside hydrolase comprising one or more domains selected from the group consisting of SEQ ID NO: 1-155; SEQ ID NO: 1095-1309; and SEQ ID NO: 3851-3972; and SEQ ID NO: 9755-11844. In one embodiment, the invention comprises an organism comprising a polynucleotide sequence which codes for a domain selected from the sequences of SEQ ID NO: 1-155; SEQ ID NO: 1095-1309; and SEQ ID NO: 3851-3972; and SEQ ID NO: 9755-11844.

The scope of the invention encompasses methods of using engineered proteins comprising lignocellulose degrading enzymes to facilitate the breakdown of lignocellulosic biomass. In one such method, an engineered protein comprising a lignocellulose-degrading enzyme is produced in an engineered organism. Exemplary engineered organisms include *Saccharomyces cerevisiae, Zymomonas mobilis, Escherichia coli*, and *Clostridium thermocellum*. Systems which utilize such organisms in biofuel production are known in the art. For example, the successful heterologous expression of functional saccharization enzymes from a fungal organism in yeast has been previously demonstrated, as described in O'Malley et al., Evaluating expression and catalytic activity of anaerobic fungal fibrolytic enzymes native to *piromyces* sp E2 in *Saccharomyces cerevisiae*. Environmental Progress and Sustainable Energy 31:37-46, 2012.

In one such method, the engineered protein is produced by and is subsequently extracted from the organism. Purification or modification steps may be applied to the extracted enzyme. The enzyme may then be used in any applicable lignocellulosic bioprocessing system by contacting it with an appropriate substrate under suitable conditions for enzymatic action to occur. In one embodiment, the extracted enzyme is used as a component of an enzymatic cocktail, for example, an enzymatic cocktail used in the saccharification of cellulosic materials.

In an alternative implementation, an engineered protein comprising a lignocellulose degrading enzyme of the invention is expressed in an engineered organism, and the engineered organism is cultured with an appropriate lignocellulosic substrate to promote breakdown of the substrate.

Methods of using proteins comprising a lignocellulose degrading enzyme of the invention may be performed in any bioprocessing method, for example, in ethanol production from biomass.

Multiple Enzyme Catabolic Complexes

In another embodiment, the invention encompasses engineered enzymatic complexes. An engineered enzyme complex is a complex comprising multiple enzymes bound to a carrier or scaffold and further comprising one or more substrate binding moieties. Such multiple enzyme complexes may be used to process a substrate with high efficiency due to the presence of multiple complementary enzymatic moieties being held in proximity to the substrate by the substrate binding moieties.

Figure 1:
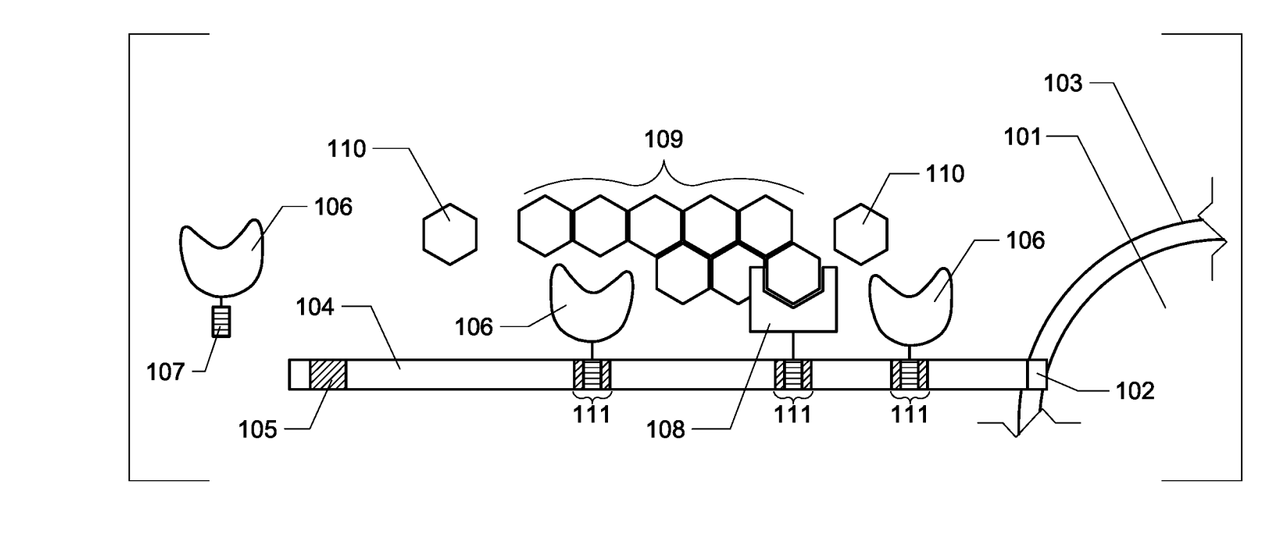

The engineered enzyme complexes of the invention are based on the bacterial cellulosome. In anaerobic microorganisms, cellulolytic enzymes are not secreted freely into the extracellular medium, as is generally the case for aerobic microbes, but instead these enzymes assemble into large (MDa) multi-protein cellulolytic complexes called cellulosomes. Cellulosomes comprise various components. A first component is a non-catalytic protein that is anchored to the cell membrane of the host cell expressing the cellulosome, typically a scaffoldin or its equivalent. The scaffoldin comprises multiple domains called cohesins, which are sites to which functional moieties will attach. The functional moieties may comprise enzymes which comprise one or more dockerin domains. The dockerin domain will selectively bind complementary cohesion domains on the scaffoldin protein with high affinity. The celluolytic complex will typically further comprise one or more carbohydrate binding moieties which bind lignocellulosic substrate. This binding keeps the substrate in proximity to the catalytic enzymes present on the cellulosome, facilitating degradation of the substrate. A conceptual depiction of a cellulosome is depicted in FIG. 1.

In one aspect, the scope of the invention encompasses what will be referred to as an engineered enzyme complex. The engineered enzyme complex comprises: a scaffold protein; one or more catalytic proteins; and one or more substrate-binding proteins. In one embodiment, the one or more catalytic proteins and one or more substrate-binding proteins are bound to the scaffold protein by cohesion-dockerin interactions with complementary dockerin and cohesion elements being present on the scaffold and on the bound moieties. An engineered enzyme complex of the invention is any enzyme complex wherein one or more component is an engineered protein of the invention. Alternatively, the engineered enzyme complex of the invention is one comprising a scaffoldin protein selected from SEQ ID NO: 27325-27327 (for example, being coded for by nucleic acid sequences SEQ ID NO: 27328-27330).

Tools and methodologies for the creation of multiple enzyme complexes and organisms expressing them are known in the art. Cellulosomes and like enzyme complexes have been successfully produced wherein the type and precise placement of enzymes is possible, for example as described in Fujita et al., Synergistic saccharification, and direct fermentation to ethanol, of amorphous cellulose by use of an engineered yeast strain codisplaying three types of cellulolytic enzyme. *Appl Environ Microbiol.* 2004 February; 70(2): 1207-12. Additional methods of producing engineered cellulosomes are described in United States Patent Application Publication Number 20150167030, entitled "Recombinant cellulosome complex and uses thereof," by Mazolli; United States Patent Application Publication Number 20130189745, entitled "Artificial cellulosome and the use of the same for enzymatic breakdown of resilient substrates," by Schwarz; and U.S. Pat. No. 9,315,833, entitled "Yeast cells expressing an exogenous cellulosome and methods of using the same," by McBride.

In one implementation of the invention, the engineered multiple enzyme complex is an artificial cellulosome designed for the efficient digestion of lignocellulosic biomass, wherein the one or more catalytic proteins comprise a plurality of proteins which degrade lignocellulosic material, e.g. glycoside hydrolase proteins, and the one or more substrate-binding proteins comprise carbohydrate binding domains.

In one embodiment, the scaffold protein of the engineered enzyme complex is a scaffoldin protein comprising multiple cohesion domains. For example, the scaffoldin protein may comprise a scaffoldin protein selected from the group consisting of SEQ ID NO: 27325-27327. In another embodiment, the artificial cellulosome comprises a dockerin domain. In one embodiment, the dockerin domain comprises a dockerin domain selected from the group consisting of: SEQ ID NO: 1420-3705 and SEQ ID NO: 6590-8910. In another embodiment, the artificial cellulosome comprises one or more carbohydrate binding domains. For example, the carbohydrate binding domain may comprise a carbohydrate binding domain selected from the sequences of: SEQ ID NO: 1061-1062; SEQ ID NO: 1325-1333; SEQ ID NO: 1378-1419; SEQ ID NO: 3706-3850; SEQ ID NO: 3973-6254; and SEQ ID NO: 9480-9605. In one embodiment, the artificial cellulosome of the invention comprises one or more glycoside hydrolase proteins comprising one or more domains selected from the sequences of SEQ ID NO: 1-155; SEQ ID NO: 1095-1309; and SEQ ID NO: 3851-3972; and SEQ ID NO: 9755-11844.

The scope of the invention further extends to nucleic acid sequences which code for the various elements of the artificial cellulosomes. The scope of the invention further encompasses engineered organisms which express the various elements of the artificial cellulosome. The scope of the invention further encompasses methods of using such engineered organisms in the digestion of lignocellulosic biomass. It will be understood that the artificial cellulosomes of the invention comprise or are expressed in combination with anchoring moieties, secretory signals and other elements required for the expression, secretion, and assembly of cellulosomes, as known in the art.

The artificial cellulosomes of the invention enable components from two or more species to be advantageously combined. Enzymes from non-fungal species can be utilized in anaerobic fungal cellulosomes, or enzymes from anaerobic fungi can be used in non-fungal cellulosomes. For example, in one implementation, the novel dockerin domains of the invention derived from anaerobic fungi may be fused with enzymes or carbohydrate-binding moieties from other species, such as from yeast or aerobic bacteria, and these combined elements can be bound to scaffoldins from anaerobic fungi. In another implementation, dockerins from other species could be fused to catalytic proteins or carbohydrate binding domains from anaerobic fungi, facilitating the inclusion of these anaerobic fungal proteins in synthetic cellulosomes of other species. This exchange of enzymatic elements from divergent species aids in the creation of novel artificial cellulosomes having extended enzymatic capabilities beyond those of wild type enzymatic complexes. Such hybrid systems can, with a single organism, recapitulate digestive processes in the complex environment of the rumen, where fungal, yeast, and bacterial strains work in concert to digest complex biomass.

It will be understood that the engineered enzyme complexes of the invention are not limited to multiple enzyme complexes which degrade lignocellulosic material, and may be designed for efficient enzymatic action of any kind on any substrate, as determined by the selection of suitable catalytic enzymes and substrate-binding moieties.

Polyketide Synthases

A very large number of important drugs and biologically active compounds are from the group called polyketides. Polyketides are structurally diverse compounds created by multi-domain enzymes or enzyme complexes called polyketide synthases (PKSs). PKSs proteins are composed of various peptide domains, each of which has a defined function. Various classes of PKSs are known, including Type I, Type II, and Type III PKSs. The Type I PKSs may be classified as either iterative or modular.

The iterative PKSs comprise a single module. The creation of a polyketide is initiated by binding a starting material to the acyl-transferase (AT) domain, the starting material typically being Acetyl-CoA or malonyl-CoA. The bound starting material is then shuttled to the KS domain by an acyl carrier protein (ACP). An extender material, typically malonyl-CoA is then loaded into the complex by the AT domain and is added to the starter material by a condensation reaction catalyzed by the ketosynthase (KS domain). Additional domains may introduce modifications to the bound chain by catalytic action. Additional extension reactions and modification reactions occur until the polyketide chain has reached its final length, which is specific for each type of iterative PKS. The mechanisms by which final length is controlled are not known. When the polyketide has reached its final length, a thioesterase (TE) domain releases the completed polyketide. Thus, such PKSs are called "iterative" because the final product polyketide is produced in an iterative fashion by the repeated action of the domains to lengthen and modify the growing polyketide chain. The various enzymatic domains of the iterative PKSs are not always used in each cycle, allowing for more variability in final product composition.

In contrast, modular PKSs have multiple repeating modules, arranged from the N-terminal end of the PKS towards the C-terminal end. In each module, the AT, ACP, and KS domains are repeated, and each module also contains its own combination of catalytic domains. Chain elongation is initiated at the N-terminal end in the first module, and the growing chain is passed from module to module towards the C-terminal end, undergoing a single elongation and one or more enzymatic modifications at each step. At the C-terminal module, a thioesterase (TE) domain releases the completed polyketide.

Just as PKS domains can interact with one another, PKSs can interact, or form hybrid complexes, with non-ribosomal peptide synthases to form active compounds (e.g. the anticancer compound epothilone).

Various classes of enzymatic PKS domain are known, including:
- keto reductase (KR) domains, which reduces ketone groups to hydroxyl groups;
- dehydratase domains (DH), which reduces hydroxyl groups to enoyl groups;
- enoyl reductase (ER) domains, which reduce enoyl groups to alkyl groups;
- methyltransferase (MT) domains, which transfer methyl groups to the growing polyketide;
- sulfohydrase domains (SH); and
- product template domains, which determine the folding pattern of the polyketide backbone.

Additional non-PKS catalytic domains that work in tandem with PKS domains include aminotransferases, pyridoxal-phosphate transferases and HMG-CoA synthases.

The specificity of substrates and products for the domains varies, as well as their order within PKSs. Accordingly, the different combinations the order of enzymatic domains within the PKS modules, and the different arrangements of modules within modular PKSs means that these enzymes can be configured to produce an immense range of final products.

The released polyketide may then be further modified by the action of additional enzymes, for example the addition of carbohydrate moieties or methyl groups. The further complexity of PKS systems enables even greater diversity of products, for example, two iterative PKSs can interact to form a common product (for example as in the synthesis of zearalenone). A PKS may also be fused with another enzyme to form a single enzyme (for example as known in the synthesis of fusarin C).

Accordingly, PKSs, due to their modular nature, including multiple domains arranged within a module, and multiple modules within an enzyme, present a potential platform for the synthesis of myriad biological products.

Engineered PKS's

Engineered PKS systems are known in the art and have been successfully utilized to create various novel end products, some of which have never been observed in nature. Various strategies exist for utilizing novel PKS enzymes, PKS modules, or PKS domains in the creation of diverse, potentially bioactive molecules. Exemplary PKS engineering techniques are described in U.S. Pat. No. 9,334,514, entitled "Hybrid polyketide synthases," by Fortman et al.; U.S. Pat. No. 8,709,781, entitled "System and method for the heterologous expression of polyketide synthase gene clusters," by Boddy et al.; and United States Patent Application Publication Number 20130067619, entitled "Genes and proteins for aromatic polyketide synthesis," by Page and Gagne.

The current state of PKS engineering allows for the recombination and swapping of various PKS enzymes, modules, and domains, enabling novel means of synthesizing compounds using engineered enzyme systems. Accordingly, there is a need in the art for PKS enzymes, modules, and domains with novel functions, which such elements may be employed in engineered PKS systems. The novel PKS gene and protein sequences provide the art with novel tools for the creation of engineered PKS synthesis systems and enable the creation of novel compounds.

In one aspect, the scope of the invention encompasses engineered proteins comprising engineered PKS enzymes. The engineered PKS enzyme of the invention may comprise a modular PKS or an iterative PKS. In one embodiment, the engineered PKS enzyme of the invention comprises an acyl transerase domain. For example the engineered PKS may comprise an acyl transferase domain selected from the sequences of SEQ ID NO: 465-578; SEQ ID NO: 768-798; and SEQ ID NO: 12479-12509. In one embodiment, the engineered PKS comprises an acyl carrier protein domain. For example, the acyl carrier protein domain may comprise an acyl carrier domain selected from the sequences of SEQ ID NO: 604-767 and SEQ ID NO: 12463-12473. In one embodiment, the engineered PKS comprises a ketosynthase domain. For example, the ketosynthase domain may comprise a ketosynthase domain selected from the sequences of SEQ ID NO: 12546-12579. In one embodiment, the engineered PKS comprises a thioesterase domain. For example, the thioesterase domain may comprise a thioesterase domain selected from the sequences of SEQ ID NO: 13417-13449. In one embodiment, the engineered PKS comprises a ketoreductase domain. For example, the ketoredudctase domain may comprise a ketoreductase domain selected from the sequences of SEQ ID NO: 12028-12043 and SEQ ID NO: 12526-12545. In one embodiment, the engineered PKS comprises a dehydratase domain. For example, the dehydratase domain may comprise a dehydratase domain selected from the sequences of SEQ ID NO: 12129-12152 and SEQ ID NO: 12771-12785. In one embodiment, the engineered PKS comprises an enoyl reductase domain. For example, the enoly reductase domain may comprise an enoyle reductase domain selected from the sequences of SEQ ID NO: 12510-12525 and SEQ ID NO: 13651-13654. In one embodiment, the engineered PKS of the invention comprises a product template domain. For example, the product template domain may comprise a product template domain selected from the sequences of SEQ ID NO: 12786-12787. The scope of the invention further encompasses engineered proteins which are not PKS enzymes, but which contain any of the aforementioned PKS domains.

The scope of the invention further includes engineered accessory enzymes, which, as used herein, are engineered proteins with functions accessory to PKS enzymes. In one embodiment, the engineered protein comprises an aminotransferase domain selected from SEQ. ID NO: 973-982. In one embodiment, the engineered protein comprises a pyridoxal-phosphate transferase domain selected from SEQ. ID NO 12862-12879. In one embodiment, the engineered protein comprises a HMG-CoA synthase domain selected from SEQ. ID NO 11883-11891.

The scope of the invention further encompasses nucleic acid constructs which code for any of the aforementioned engineered PKS enzymes or engineered accessory enzymes. Furthermore, the scope of the invention encompasses engineered organisms which express any of the aforementioned engineered PKS enzymes or which comprise a nucleic acid construct coding therefor. Exemplary engineered PKS organisms include fungal species, bacterial species, yeast species, or plant species. The scope of the invention further encompasses methods of creating complex molecules, including polyketides, utilizing the engineered PKS enzymes and/or organism expressing such engineered PKS enzymes, wherein suitable substrates are exposed to such engineered PKS enzymes and/or organism expressing such engineered PKS enzymes under conditions which facilitate the synthesis of desired end-products.

Biofuel Production Using Novel Anaerobic Fungal Strains

Lignocellulosic material, or biomass, is a renewable and abundant material and represents a potential feedstock for energy and chemical production. However, the sugars contained in lignocellulosic materials are locked in a complex of lignin, hemicellulose and cellulose and other plant cell wall components. Currently, to extract fermentable sugars from these recalcitrant feedstocks, lignin and hemicellulose must be separated from the biomass prior to converting cellulose into monosaccharides. As a result, bioprocessing of crude biomass entails energy-intensive pretreatment steps, and the addition of an expensive and often inefficient cocktails of cellulolytic enzymes.

In contrast, anaerobic gut fungi that are resident in the gut of herbivores routinely and efficiently degrade cellulose in complex, lignin-rich biomass. This is achieved through both mechanical and enzymatic processes: colonizing fungi develop a highly branched rhizoidal network, or rhizomycelium, that penetrates and exposes the substrate to attack by secreted cellulases. Importantly, this unique invasive strategy for plant cell wall degradation enables gut fungi to colonize and decompose complex cellulosic feedstocks. Anaerobic gut fungi degrade plant particulates of dissimilar sizes at nearly the same rate, whereas the degradation rates of eubacterial populations steadily decrease with increasing particle size. Therefore, anaerobic gut fungi may serve as a means to degrade diverse biomass feedstocks to useful bioenergy compounds, without the need for expensive pretreatment, greatly reducing the cost and increasing the efficiency of biomass conversion to useful products.

Accordingly, there is a need in the art for novel organisms capable of efficient conversion of biomass to usable fuel materials, and for methods of culturing such organisms. The four previously undescribed species of anaerobic fungal gut organisms described herein fulfill this need in the art, being capable of breaking down plant material to produce ethanol, hydrogen, and other useful materials. Grown under anaerobic culture conditions, each of the four organisms is capable of degrading a wide range of lignocellulosic materials. For example, the organisms can metabolize reed canary grass, glucose, fructose, avicel, and filter paper, demonstrating an ability to break down a wide range of biomass materials.

In addition to cellulosomes, which convert plant material into fermentable sugars, anaerobic fungi possess hydrogenosomes that convert the released sugars to hydrogen gas following glycolysis. Hydrogenosomes are intracellular membrane-bound organelles that are analogous to the mitochondria of aerobic microbes. In general, they metabolize malate and pyruvate to $H_2$, $CO_2$, formate, and acetate, generating energy in the form of ATP. The four novel organisms described herein are each capable of hydrogen production from a range of feedstocks.

Accordingly, in one aspect, the invention comprises the use of *Piromyces finnis*, *Neocallimastix californiae*, *Anaeromyces robustus*, and/or *Neocallimastix* sp S4 in the conversion of biomass feedstocks into ethanol, hydrogen, and other useful materials. The basic process of the invention comprises introducing biomass feedstocks into a bioreactor vessel wherein culture conditions amenable to organism growth and metabolism are maintained, allowing colonization and digestion of biomass by the organisms, and ongoing or subsequent harvesting of end-products.

Anaerobic bioreactors and fungal bioreactors are known in the art. For example, exemplary fungal and/or anaerobic bioreactors are described in: Moreira et al., Fungal Bioreactors: Applications to White-Rot Fungi, Reviews in Environmental Science and Biotechnology, 2003, Volume 2, Issue 2-4, pp 247-259; Martin, An Optimization Study of a Fungal Bioreactor System for the Treatment of Kraft Mill Effluents and Its Application for the Treatment of TNT-containing Wastewater, in Bioreactors, Auburn University Press, 2000; Palma et al., Use of a fungal bioreactor as a pretreatment or post-treatment step for continuous decolorisation of dyes, 1999, WATER SCIENCE AND TECHNOLOGY; 40, 8; 131-136; US Patent Publication Number US 20100159539 A1, Methods and systems for producing biofuels and bioenergy products from xenobiotic compounds, by Ascon; China Patent Publication 101374773, Method and bioreactor for producing synfuel from carbonaceous material, by Khor; and US Patent Publication Number 20100196994 A1, Fungi cultivation on alcohol fermentation stillage for useful products and energy savings, by van Leeuwen. Bioreactor designs amenable to the growth of the gut fungi described herein may be readily developed utilizing knowledge of the growth conditions optimal for anaerobic gut fungi growth and activity. The invention encompasses the use of any type of bioreactor design, including batch reactors, flow-through reactors, and other bioreactor designs known in the art.

Anaerobic fungi are may be grown under substantially anaerobic conditions. Optimal temperatures for the growth and biomass digestive activity of such organisms is in the range of 25-40 C, preferably in the range of 30-40 C. Cultures may be grown without agitation, on soluble or insoluble carbon sources, under a head space of 100% $CO_2$ gas. Liquid culture medium is preferred for growth and maintenance of the anaerobic fungi.

The culture media used to grow anaerobic fungi may be any known in the art, for example formulations based on those used for the cultivation of rumen bacteria. For the most part, they are complex, non-defined media (pH 6.5-6.8) and contain up to 15% (v/v) clarified rumen fluid, but chemically defined media can be used as well, as described in Marvin-Sikkema, F. D., Lahpor, G. A., Kraak, M. N., Gottschal, J. C., Prins, R. A., Characterization of an anaerobic fungus from llama faeces. *J. Gen. Microbiol.* 1992, 138, 2235-2241. Although phosphate buffers may be used, a preferred buffer is bicarbonate with $CO_2$ in the head space contributing to the buffering system. Chemical reducing agents (e.g., sodium sulfide and/or L-cysteine hydrochloride) are added to culture media pre- or post-autoclaving, after the majority of the $O_2$ has been removed from culture solutions by boiling and gassing with $CO_2$. These procedures ensure that low oxygen levels of the culture medium are maintained such that anaerobic fungal growth can be supported.

The methods of the invention encompass various steps. In a first step, biomass is fed into the bioreactor. Any form of cellulosic or lignocellulosic material may be utilized in the bioreactors and methods of the invention. Biomass includes, but is not limited to, herbaceous material, agricultural residues, forestry residues, municipal solid wastes, waste paper, and pulp and paper mill residues. Exemplary feedstocks include corn stover, canary reed grass, swtichgrass, *Miscanthus*, hemp, poplar, willow, sorgum, sugarcane, bamboo, eucalyptus. Additional feedstocks include byproducts of industrial processes, such as pulping liquor (a byproduct of paper production).

Generally, it is preferred that the biomass feedstocks utilized in the processes of the invention be pre-processed to some degree prior to digestion by the fungal organisms. Preprocessing steps include grinding or other mechanical treatments which break the biomass into small particulates that may be more easily colonized and digested by the fungal organisms. Particulates in the range of 0.1 to 10 mm diameter, for example, may be used.

The biomass material is then inoculated with one or more fungal strains selected from the group consisting of *Piro-*

*myces finnis, Neocallimastix californiae, Anaeromyces robustus*, and *Neocallimastix* sp S4. Exemplary inoculant material includes particulate material which has been colonized by the fungal organism(s). As opposed to free zoospores, using such material as the starting inoculum leads to more vigorous growth and a substantial reduction in culture lag. The inoculated biomass is then allowed time to digest. The precise digestion time will vary depending on (1) the composition and lability of the feedstock; (2) the particulate size of the feedstock; (3) the concentration of inoculant; and (4) the specific bioreactor design. End-products of the digestion may be removed from the bioreactor at set intervals, continuously, or at the end of the digestion process. Removal of ethanol may be accomplished using methods known in the art for separation of ethanol from fermentation broth. Likewise, evacuation of hydrogen gas produced by the digestion may be accomplished utilizing means known in the art.

Working cultures of anaerobic fungi may require frequent sub-culturing in order to retain their viability. Most batch cultures remain viable for 5 or 15 days in media containing soluble (glucose) or particulate (reed canary grass) substrates, respectively. Frequent sub-culturing intervals of 2-7 days with growth on particulate substrates are generally employed to ensure the continued production of viable cultures.

The processes of the invention may optionally further encompass the co-culture of the described anaerobic gut fungi with other organisms to promote optimal production of bioenergy materials. For example, co-culture of anaerobic gut fungi with highly effective anaerobic fermenting organism, yeast or bacterial strains can result in an optimized system with efficient saccharization and fermentation. Similarly, production of specific end-products can be enabled by co-inoculation with organisms that convert the products of fungal digestion to other materials. For example, production of hydrogen through fungal hydrogenosome activity allows other microbes to reduce $H_2$ to the more energetically favorable methane gas. Co-culture with methane-producing organisms such as Archaea shifts end-product formation towards increased methane and acetate production, with a corresponding decrease in lactate, succinate, hydrogen and ethanol accumulation. In another embodiment, co-culture of anaerobic gut fungi with methanogens can be performed, which can significantly enhance the cellulose hydrolysis activity of the anaerobic fungi.

EXAMPLES

Example 1

Sequence Identification Fresh fecal material was collected from farm animals. Specimens were isolated from 5×10-fold serial dilutions of fecal matter in anaerobic buffer medium. Each dilution was then supplemented with 30 µg/ml chloramphenicol and grown in anaerobic medium containing milled reed canary grass at 39° C. to enrich for gut fungi. Enrichment cultures that were positive for fungal, but not bacterial or protist, growth after 5-10 days as determined by the generation of fermentation gases without an increase in culture turbidity were further subcultured. To generate unique fungal isolates, actively growing enrichment cultures were diluted up to 50-fold in serial dilutions with each dilution being subcultured for ~4 days. This isolation procedure was repeated five times until a uniform fungal morphology was observed from each specimen and a unique ITS sequence of the isolate was obtained. Subsequent phylogenetic analysis of this ITS sequence confirmed the presence of a single novel fungal isolate in each culture. The new species were named *Neocallimastix californiae*, isolated from goat feces, *Anaeromyces robustus*, isolated from sheep feces, and *Neocallimastix* sp S4, isolated from sheep feces, and *Piromyces* sp. finn, isolated from horse feces.

To identify novel sequences of interest, each strain was grown in anaerobic medium supplemented with either glucose or milled reed canary grass at 3° C. After 2 days, the biomass was harvested and the total RNA extracted using the Qiagen RNeasy kit. This RNA was then enriched for mRNA by selecting for polyadenylated RNA and made into a strand specific cDNA library (single stranded). This cDNA library was then sequenced using an Illumina HiSeq next generation sequencing platform, using a standard workflow, and the resulting data was assembled into a de novo transcriptome using the TRINITY bioinformatics platform. The assembled sequences were then annotated with the BLAST2GO package by BLAST sequence alignment against known protein sequences and protein domain hidden Markov model (HMM) scans on Interpro of all possible translations of each transcript. The results were analyzed for statistical significance and sequences of interest were noted.

Example 2

Identification and Characterization of Scaffoldin Proteins

Genomic analysis of 5 unique anaerobic fungi revealed the presence of 1600 total dockerin domain proteins (DDPs) across genera with diverse functionality, primarily related to plant carbohydrate binding and biomass degradation. These include 15 glycoside hydrolase (GH) families, 5 distinct carbohydrate-binding domains, and other functions implicated in plant cell wall modification and deconstruction including pectin modifying enzymes and expansins. 20.2% of DDPs belong to spore coat protein CotH, which are also present in bacterial cellulosomes and are speculated to also be involved in plant cell wall binding. Conversely, 12.6% represent additional GH activities that are not present in bacterial cellulosomes (GH3, GH6, and GH45). The additional β-glucosidase conferred by GH3 in particular enables fungal cellulosomes to convert cellulose directly to fermentable monosaccharides, whereas Clostridial cellulosomes produce low molecular weight oligosaccharides.

To find structural proteins that mediate assembly of DDPs, we isolated the supernatant and cellulosome fractions from three of these isolates growing on reed canary grass as a sole carbon substrate. Size-exclusion chromatography (SEC) of the cellulosome fraction showed complex formation well within the MDa range, and SDS-PAGE revealed the presence of many glycosylated proteins. Each fraction was subjected to tandem mass spectrometry and peptide sequences were mapped to their respective genomic and transcriptomic databases. Many of the proteins associated with these complexes were identified as GHs and other plant cell wall degrading enzymes. Proteins found in the cellulosome fraction were particularly enriched with NCDDs, indicating modular complex formation. Unexpectedly, all fractions also contained very large uncharacterized proteins (hereafter named ScaA) with molecular weights (MW) of approximately 700 kDa. These ScaA proteins share 32% sequence identity over at least 92% sequence length (E value=0.0) between fungal genera. ScaA orthologs were also detected in the only other sequenced gut fungal genomes, *Piromyces* sp. E2 and *Orpinomyces* sp. C1A, though the ortholog detected in O sp. C1A was incomplete likely due to fragmented genome assembly.

Sequence analysis of these proteins across all 5 sequenced genomes showed a predicted N-terminal signal sequence followed by a large extracellular repeat-rich domain, and ending with C-terminal membrane anchor. Some of these proteins also encode predicted choline binding repeats (CBRs), which are known to bind glucan in prokaryotic glucosyltransferases. Thus, one possibility is that CBRs help mediate fungal cellulosome assembly, as many cellulosome proteins are glycosylated. Closer examination of the sequences revealed the presence of a repeating amino acid sequence motif that is conserved among all of these homologues, and that occurs many times throughout these proteins. This motif is 20-30 amino acids long, typically includes with a Gly residue immediately followed by two large hydrophobic residues (most often Tyr residues) and two non-consecutive downstream Cys residues.

Because these proteins are highly represented in secretome and cellulosome fractions from these diverse species of gut fungi, we hypothesized that they share a common role in these systems, possibly in DDP assembly. We hypothesized that these proteins function as scaffolds whereby the repeating motifs act as dockerin-binding cohesins. To investigate this, we recombinantly expressed fragments of the ScaA homologues in *Escherichia coli* and performed enzyme linked immunosorbent assay (ELISA) using purified dockerin and anti-dockerin chemiluminescent secondary antibody. These results showed a strong dockerin binding signal in wells containing the scaffoldin fragment cells compared to those containing the empty vector control. As an additional control, a phenylalanine substitution to dockerin residue W28, previously identified to be critical for binding, showed significantly reduced binding activity. To determine the binding affinity of dockerin-ScaA interaction, we purified *Piromyces* ScaA fragments and performed equilibrium analysis by surface plasmon resonance (SPR) against purified fungal dockerin. This analysis revealed that a single dockerin domain interacts with the scaffoldin fragment with an approximate dissociation constant ($K_d$) of 0.7 µM and a maximum response ($R_{max}$) of 80 RU. Additionally, the W28F dockerin mutant showed significantly reduced binding affinity ($K_d$=2.0 µM, $R_{max}$=40 RU). Taken together, these results suggest that fungal scaffoldin proteins likely mediate assembly of DDPs in fungal cellulosomes.

Though limited, previous studies have shown that fungal cellulosomes are quite divergent from their bacterial counterparts. For example, NCDDs occur as tandem repeats at the N- and/or C-terminus, with the most common form being a double tandem repeat (i.e. double dockerin) at the C-terminus. Though the functional role of this motif repetition is not known, it has been previously noted that double dockerins bind to native cellulosomes more efficiently than single domains[5]. Thus, we hypothesized that increasing the number of NCDD from one to two could enhance binding affinity to the scaffoldin fragment. By ELISA, we found that the *P. finnis* single dockerin domain had higher binding affinity than the double dockerin domain. However, by SPR, the double dockerin had a comparable $K_d$, but a higher $R_{max}$ 120 RU, suggesting that the double dockerin is indeed capable of binding to more sites on the ScaA fragment than the single dockerin, which suggests that site specificity may be more subtly encoded in the different dockerin domains and cohesin repeats. Though the minimum sequence that defines a single cohesin remains to be determined, it is clear from our study that fragments of the scaffoldin encoding as few as four repeats are sufficient for dockerin assembly. Additionally, we cannot rule out that additional binding factors (e.g. glycosylation) found in native cellulosomes likely further modulate the fungal dockerin-cohesin interaction, which are lacking in this recombinant system.

It has previously been reported that dockerins are capable of binding to cellulosome fractions from other species of gut fungi, which is a marked departure from bacterial cellulosomes. In agreement with this observation, a *Piromyces* dockerin is capable of binding to intact cellulosome fractions harvested from *Anaeromyces* and *Neocallimastix* species. Thus, we tested whether this cross-species binding activity is encoded specifically within ScaA homologues. To test this, we purified single dockerin domains from all three genera of gut fungi and tested their ability to bind to all combinations of ScaA fragments. Indeed, we observed binding for all combinations tested and the binding signal was within standard error for almost all cases. Taken together, these results demonstrate that the fungal scaffoldin system is broadly conserved across the anaerobic fungal phylum, allowing for high interspecies infidelity. Therefore, it is not unreasonable to speculate that in their native environments, for example the dense microbial community of the herbivore rumen, fungal cellulosomes are a composite of enzymes from several species of gut fungi. This is in stark contrast to bacterial cellulosomes, which have high species specificity. This promiscuity may confer a selective advantage of fungi over bacteria in these environments.

In addition to the ScaA orthologs, other scaffoldin-like proteins were also detected through proteomic analysis of cellulosome-associated proteins. We tested three of these scaffoldins for dockerin binding activity and each tested positive over an empty vector control, suggesting that multiple scaffoldins likely exist in fungal cellulosomes. To search for scaffoldin-like proteins more broadly within anaerobic fungi, we developed a Hidden Markov Model (HMM) based on the repeating motif from all 6 scaffoldins biochemically verified to interact with dockerins. We found 95 unique loci in the genomes of *A. robustus, P. finnis*, and *N. californiae*, that bear a signal peptide and at least 10 cohesin repeats. Fewer loci (14) were detected in P. sp. E2 and O. sp. C1A due to fragmented genome assemblies. Significantly, no loci were found in prokaryotes (~2000 genomes) and only 1 or 2 weak hits in other fungi (~400 genomes), demonstrating this HMM is highly specific to fungal scaffoldins. These results indicate that gut fungi likely produce multiple scaffoldins for cellulosome assembly, and these scaffoldins represent a new family of genes that is unique to the early branching anaerobic fungi.

While fungal scaffoldins and their NCDD ligands are specific to gut fungi, many plant biomass degrading enzymes that encode NCDDs are of bacterial origin, which has been noted previously for a limited subset of enzymes. Indeed, all five gut fungal genomes sequenced to date have large numbers of genes that are more similar to bacterial than to eukaryotic genes (9-13%). We aligned 1600 DDPs of the 5 anaerobic fungal genomes with the 394 fungi currently deposited in JGI MycoCosm (excluding Neocallimastigomycota) and the 1774 bacteria and archaea in JGI Integrated Microbial Genomes (IMG). Of these proteins, 611 aligned better with bacterial than fungal proteins and 158 aligned exclusively with bacteria. Conversely, only 38 aligned exclusively with fungi, and 372 aligned better to fungi than to bacteria. The remaining DDPs aligned equally with IMG and MycoCosm protein (3) or did not align with either (418). To determine whether this bacterial resemblance is the result of inter-kingdom horizontal gene transfer (HGT), we queried the domains that are fused to NCDDs to extract homologous sequences from the same bacterial and fungal genomes. When possible, we built phylogenetic trees of the domain sequences. Out of 35 non-dockerin domains analyzed, 10 (29%) passed our 2 criteria of 1) greater amino acid similarity to bacterial than to fungal sequences and 2) branching with bacterial rather than fungal sequences in its phylogenetic tree with >70% bootstrap support. The list of domains with an HGT signature includes 9 CAZyme domains as well as the spore coat domain. However, this analysis does not inform us as to the direction of any possible HGT events. Subjecting NCDDs to the same analysis showed that there are no similar sequences in IMG at all, suggesting that many DDPs may be fusions between native fungal and horizontally transferred bacterial components. Intriguingly, we found 12 fungal-bacterial homolog pairs where the bacterial protein is also a bacterial dockerin-domain protein. However, the sequence similarity between each pair of homologs encompasses only the catalytic domain and does not extend into the respective dockerin domains.

Over the past several decades, characterization of cellulosomes in fungi has been elusive, with multiple studies suggesting conflicting scaffolding schemes. Here, next-generation sequencing combined with functional proteomics uncovered a new family of genes that likely serve as scaffoldins in the cellulosomes of anaerobic fungi. The evidence for this is 3-fold: (1) scaffoldins appear among the most represented proteins in supernatant and cellulosome fractions in three diverse isolates of gut fungi, and their amino acids sequences encode hallmarks of a membrane-anchored scaffoldin molecule, including an N-terminal secretion motif, a C-terminal membrane anchor, and repeating amino acid motif in between. These scaffoldins are encoded in all sequenced Neocallimastigomycota (representing 4 of the 8 genera of gut fungi identified to date) and absent in other fungi. (2) Expression of repeat-containing scaffoldin fragments shows robust interaction with purified dockerins by ELISA. (3) This dockerin-scaffoldin interaction is biologically significant ($K_d$≈0.7 uM) as measured by SPR, whereas a mutated dockerin derivative significantly reduced binding activity. Taken together, the identification of a new dockerin-binding protein scaffold from fungi opens the way for exploitation of this modular interaction for synthetic biology and substrate channeling. Finally, the powerful degradation activity of gut fungi is provided by the diverse functionality of its constituents, with 50 unique protein families of bacterial and fungal origin, and the assembly of these constituents onto scaffoldin molecules into cellulosome-like complexes. Perhaps the most intriguing observation from this study is that fungal dockerins and their scaffoldin ligands have no sequence similarity to their bacterial counterparts. Thus, it is possible that the cellulosome-based strategy for plant cell wall degradation evolved in anaerobic gut fungi independently of bacteria. This suggests that co-localizing plant cell wall degrading enzymes is so effective that nature has evolved it on more than one occasion.

Example 3

Characterizing the Production of Secondary Metabolites in Anaerobic Fungi

In order to better understand the production of secondary metabolites by the anaerobic fungi of the invention, bioinformatics tools and analytical tools were employed. It was determined that numerous genes involved in the production of secondary metabolites were actively transcribed in *Piromyces finnis, Anaeromyces robustus*, and *Neocallimastix californiae*. Genes involved in secondary metabolite production included PKS genes as well as genes involved in the synthesis of nonribosomal peptides, terpenes, fatty acids, bacteriocins, and others.

Additionally, LC-MS/MS analysis of fungal products was performed, and a large number of peaks were observed, each corresponding to a composition having unique mass and charge. These results provide promising experimental evidence that secondary metabolites are produced in abundance by these anaerobic fungi.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11021524B2). An electronic copy of the "Sequence Listing" will also be available from the USPTO upon request and payment of the fee set forth in 37 CFR 1.19(b)(3).

What is claimed is:

1. A hydrogen producing organism, wherein
the hydrogen producing organism is engineered to expresses a glycoside hydrolase protein comprising a protein having at least 95% sequence identity to SEQ ID NO: 11184.

2. The hydrogen producing organism according to claim 1, wherein
the hydrogen producing organism is an organism selected from the group consisting of *Saccharomyces cerevisiae, Zymomonas mobilis, Escherichia coli, Clostridium thermocellum*, and a fungal species.

3. The hydrogen producing organism according to claim 1, wherein
the hydrogen producing organism further expresses one or more catalytic enzymes capable of digesting lignocellulosic biomass.

4. The hydrogen producing organism according to claim 1, wherein
the hydrogen producing organism is combined into a co-culture with a lignocellulosic biomass digesting organism expressing at least one or more catalytic enzymes capable of digesting lignocellulosic biomass in a bioreactor vessel.

5. The hydrogen producing organism according to claim 1, wherein
the engineered protein having at least 95% sequence identity to SEQ ID NO: 11184 is produced and is subsequently extracted from the hydrogen producing organism, and whereby the engineered protein further comprises a dockerin domain.

6. The hydrogen producing organism according to claim 1, wherein
the hydrogen producing organism further expresses a dehydrogenase protein.

7. The hydrogen producing organism according to claim 5, wherein
the dockerin domain is fused with a carbohydrate-binding element from an organism selected from a bacterial species, a yeast species, a fungal species, or a plant species.

8. The hydrogen producing organism according to claim 4, wherein
the co-culture is further comprises a yeast strain or bacterial strain, or a combination of a yeast strain with a bacterial strain.

9. The hydrogen producing organism according to claim 1, wherein
the hydrogen producing organism is a species selected from the group consisting of a bacterial species, a yeast species, a fungal species, or a plant species.

10. The hydrogen producing organism according to claim 9, wherein
the protein having at least 95% sequence identity to SEQ ID NO: 11184 is produced by and is subsequently extracted from the hydrogen producing organism.

11. The hydrogen producing organism according to claim 10, wherein
the engineered organism expresses an engineered multiple enzyme complex comprised of the protein having at least 95% sequence identity to SEQ ID NO: 11184.

12. The hydrogen producing organism according to claim 1, wherein
the hydrogen producing organism is a cultured anaerobic fungal species selected from the group consisting of *Piromyces* finnis, *Neocallimastix* californiae, *Anaeromyces robustus*, and *Neocallimastix* sp S4.

* * * * *